(12) United States Patent
Honda et al.

(10) Patent No.: US 9,318,312 B2
(45) Date of Patent: Apr. 19, 2016

(54) ULTRAVIOLET LIGHT GENERATING TARGET, ELECTRON-BEAM-EXCITED ULTRAVIOLET LIGHT SOURCE, AND METHOD FOR PRODUCING ULTRAVIOLET LIGHT GENERATING TARGET

(75) Inventors: Yoshinori Honda, Hamamatsu (JP); Fumitsugu Fukuyo, Hamamatsu (JP); Yuji Kasamatsu, Hamamatsu (JP); Takashi Suzuki, Hamamatsu (JP); Takeaki Hattori, Hamamatsu (JP); Koji Kawai, Hamamatsu (JP); Shucheng Chu, Hamamatsu (JP); Hiroyuki Taketomi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 146 days.

(21) Appl. No.: 14/113,383

(22) PCT Filed: Apr. 24, 2012

(86) PCT No.: PCT/JP2012/060976
§ 371 (c)(1),
(2), (4) Date: Oct. 23, 2013

(87) PCT Pub. No.: WO2012/147744
PCT Pub. Date: Nov. 1, 2012

(65) Prior Publication Data
US 2014/0048721 A1 Feb. 20, 2014

(30) Foreign Application Priority Data
Apr. 25, 2011 (JP) ................. 2011-097501

(51) Int. Cl.
*G01J 1/42* (2006.01)
*G01N 21/64* (2006.01)
(Continued)

(52) U.S. Cl.
CPC ............. *H01J 63/02* (2013.01); *C09K 11/7774* (2013.01); *H01J 29/20* (2013.01); *H01J 63/06* (2013.01); *G01J 1/429* (2013.01); *G01N 21/64* (2013.01); *H01J 63/04* (2013.01)

(58) Field of Classification Search
CPC .................................. G01N 21/64; G01J 1/429
See application file for complete search history.

(56) References Cited

U.S. PATENT DOCUMENTS

| 5,399,499 | A * | 3/1995 | Paz-Pujalt et al. ............. 436/165 |
| 2010/0289435 | A1 * | 11/2010 | Kita .............................. 315/363 |
| 2014/0034853 | A1 | 2/2014 | Honda et al. |

FOREIGN PATENT DOCUMENTS

| EP | 1 816 241 | 8/2007 |
| EP | 1 873 226 | 1/2008 |

(Continued)

OTHER PUBLICATIONS

U.S. Office Action dated Apr. 10, 2014 that issued in U.S. Appl. No. 14/113,398 including Double Patenting Rejections on pp. 2-3.

(Continued)

*Primary Examiner* — Christine Sung
(74) *Attorney, Agent, or Firm* — Drinker Biddle & Reath LLP

(57) ABSTRACT

An ultraviolet light generating target 20 includes a substrate 21 made of sapphire, quartz, or rock crystal; and a light-emitting layer 22 that is provided on the substrate 21 and that generates ultraviolet light upon receiving an electron beam. The light-emitting layer 22 includes powdered or granular Pr:LuAG crystals. By using such a light-emitting layer 22 as the target, the ultraviolet light generating efficiency can be increased more remarkably than when a Pr:LuAG single crystal film is used.

11 Claims, 23 Drawing Sheets

(51) Int. Cl.
*H01J 63/02* (2006.01)
*H01J 29/20* (2006.01)
*H01J 63/06* (2006.01)
*C09K 11/77* (2006.01)
*H01J 63/04* (2006.01)

(56) References Cited

FOREIGN PATENT DOCUMENTS

| | | |
|---|---|---|
| JP | 2006-520836 A | 9/2006 |
| JP | 2006-335915 A | 12/2006 |
| JP | 2007-077280 | 3/2007 |
| JP | 2007-294698 A | 11/2007 |
| JP | 2008-024549 | 2/2008 |
| JP | 2009-227794 A | 10/2009 |
| JP | 2009-238415 A | 10/2009 |
| JP | 2009-256596 | 11/2009 |
| JP | 2010-235388 A | 10/2010 |
| JP | 2011-055898 | 3/2011 |
| WO | WO 2006/016711 | 2/2006 |
| WO | WO-2006/049284 A1 | 5/2006 |
| WO | WO 2007/116331 | 10/2007 |
| WO | WO-2009/031584 A1 | 3/2009 |
| WO | WO-2010/097731 A1 | 9/2010 |
| WO | WO 2014184038 A1 * | 11/2014 |

OTHER PUBLICATIONS

Zhao Jiangbo et al., "Synthesis and luminescent properties of Pr-doped $Lu_3Al_5O_{12}$ translucent ceramic", Journal of Rare Earths 27, Jun. 30, 2009, p. 376-380.

Sargsyan, Ruben, et al., "Optical and Structural Properties of $Lu_3Al_5O_{12}$:$Pr^{3+}$ Scintillator Crystals," International Conference on Laser Physics 2010, SPIE, 1000 20th St., Bellingham, WA 98225-6705, vol. 7998, No. 1, Oct. 29, 2010, pp. 1-6.

Yuriy, Zorenko, et al., "LuAG:Pr, LuAG:La and LuAP:Ce Thin Film Scintillators for Visualisation of X-ray Images," Proceedings of SPIE, vol. 7310, Apr. 30, 2009, pp. 731007 to 731007-8.

Plewa, J., et al., "On the Luminescence of $Lu_{3-x}Pr_xAl_5O_{12}$ Ceramic Bodies," Materialy Ceramiczne/Ceramic Materials, vol. 60, No. 4, 2008, pp. 229-233.

\* cited by examiner (a)

(b)

(c)

(a)

(b)

(a)

(b)

(a)

(b)

(a)

(b)

(a)

(b)

(a)

(b)

(a)

(b)

(a)

(b)

(a)

(b)

(a)

(b)

ULTRAVIOLET LIGHT GENERATING TARGET, ELECTRON-BEAM-EXCITED ULTRAVIOLET LIGHT SOURCE, AND METHOD FOR PRODUCING ULTRAVIOLET LIGHT GENERATING TARGET

TECHNICAL FIELD

The present invention relates to an ultraviolet light generating target, an electron-beam-excited ultraviolet light source, and a method for producing the ultraviolet light generating target.

BACKGROUND ART

Patent Literature 1 describes the use of a single crystal containing praseodymium (Pr) as a material of a scintillator used in a PET apparatus. Furthermore, Patent Literature 2 describes a technique relating to an illumination system for achieving white light by converting the wavelength of the light emitted from a light emitting diode by using a fluorescent material.

CITATION LIST

Patent Literature

Patent Literature 1: WO2006/049284
Patent Literature 2: Japanese Translation of International Application Publication No. 2006-520836

SUMMARY OF INVENTION

Technical Problem

Conventionally, electron tubes such as mercury-xenon lamps and heavy hydrogen lamps have been used as an ultraviolet light source. However, these ultraviolet light sources have a low luminous efficiency and are large in size, and at the same time, there are issues from the viewpoint of stability and service life. On the other hand, as another ultraviolet light source, there is available an electron-beam-excited ultraviolet light source having a structure in which ultraviolet light is excited by irradiating a target with an electron beam. The electron-beam-excited ultraviolet light sources are expected to be used in the optical measurement field by taking advantage of the high stability, and used for sterilization and disinfection purposes by taking advantage of the low power consumption, or used as a light source in medical treatment and bio-chemistry using high wavelength selectivity. Furthermore, another advantage of the electron-beam-excited ultraviolet light source is lower power consumption than a mercury lamp, or the like.

Furthermore, in recent years, a light emitting diode that can output light in the ultraviolet region, that is, light having a wavelength of 360 nm or less, has been developed. However, a problem arises that the intensity of the light output from such a light emitting diode is still small, and increasing the area of the light-emitting surface is difficult with a light emitting diode, and therefore, the usage becomes limited. In contrast, the electron-beam-excited ultraviolet light source can generate ultraviolet light of sufficient intensity, and furthermore, by increasing the diameter of the electron beam with which the target is irradiated, ultraviolet light having a uniform intensity can be output across a large area.

However, even in the electron-beam-excited ultraviolet light source, a further improvement in the ultraviolet light generating efficiency is required. An object of the present invention is to provide an ultraviolet light generating target, an electron-beam-excited ultraviolet light source, and a method for producing the ultraviolet light generating target, with which it is possible to improve the ultraviolet light generating efficiency.

Solution to Problem

In view of the above-described problems, the present inventors thought of using $(Pr_xLu_{1-x})_3Al_5O_{12}$ (Pr:LuAG Praseodymium doped lutetium aluminum garnet, where the range of x is $0<x<1$) as the ultraviolet light generating target. However, it was found that when a Pr:LuAG crystal such as that described in the prior art document is used, it is difficult to achieve sufficient ultraviolet light generating efficiency. In contrast, as a result of tests and research by the present inventors, it was found out that by converting the Pr:LuAG crystal to a powdered or granular form, and then forming it into the shape of a film, the ultraviolet light generating efficiency could be increased more remarkably than when a Pr:LuAG single crystal was used. That is, based on the ultraviolet light generating target according to an embodiment, the ultraviolet light generating efficiency can be improved by including a substrate made of sapphire, quartz, or rock crystal (crystals of silicon oxide), and a light-emitting layer that is provided on the substrate and that generates ultraviolet light upon receiving an electron beam, such that the light-emitting layer includes powdered or granular Pr:LuAG crystals.

In the ultraviolet light generating target, the thickness of the light-emitting layer may be 0.5 μm or more and 30 μm or less. According to tests and research by the present inventors, when the light-emitting layer containing powdered or granular Pr:LuAG crystals has such a thickness, the ultraviolet light generating efficiency can be increased more effectively.

In the ultraviolet light generating target, the median diameter of the Pr:LuAG crystals in the light-emitting layer may be 0.5 μm or more and 30 μm or less. According to tests and research by the present inventors, when the light-emitting layer containing powdered or granular Pr:LuAG crystals has such a particle diameter, the ultraviolet light generating efficiency can be increased more effectively.

In the ultraviolet light generating target, the surface of the Pr:LuAG crystals may be covered with a crystalline melting layer that is melted by heat treatment and then solidified again. In such a case, by the crystalline melting layer, the Pr:LuAG crystals may fuse with each other, and the Pr:LuAG crystals and the substrate may also fuse with each other.

The electron-beam-excited ultraviolet light source according to one embodiment includes any of the above ultraviolet light generating targets, and an electron source that provides an electron beam to the ultraviolet light generating target. According to the present electron-beam-excited ultraviolet light source, by including any of the above ultraviolet light generating targets, the ultraviolet light generating efficiency can be improved.

In the method for producing the ultraviolet light generating target according to one embodiment, by depositing powdered or granular Pr:LuAG crystals on a substrate made of sapphire, quartz, or rock crystal, and then performing heat treatment for the Pr:LuAG crystals, surfaces of the Pr:LuAG crystals are melted and then solidified again to form a crystalline melting layer. According to the method for producing the ultraviolet light generating target, the Pr:LuAG crystals fuse with each other, and the Pr:LuAG crystals and substrate also fuse with each other by the crystalline melting layer, and therefore, the mechanical strength of the light-emitting layer can be improved, and the light-emitting layer can be prevented from being peeled off from the substrate. In the present production method, the temperature of heat treatment is preferably between 1400° C. and 2000° C.

Advantageous Effects of Invention

According to the ultraviolet light generating target, the electron-beam-excited ultraviolet light source, and the method for producing ultraviolet light generating target of the present invention, the ultraviolet light generating efficiency can be improved.

DESCRIPTION OF EMBODIMENTS

Hereinafter, an embodiment of an ultraviolet light generating target, an electron-beam-excited ultraviolet light source, and a method for producing the ultraviolet light generating target according to the present invention are explained in detail with reference to the attached drawings. Note that in the description of drawings, the same reference sign is given to the same element, and duplicate explanations are omitted.

Figure 1:
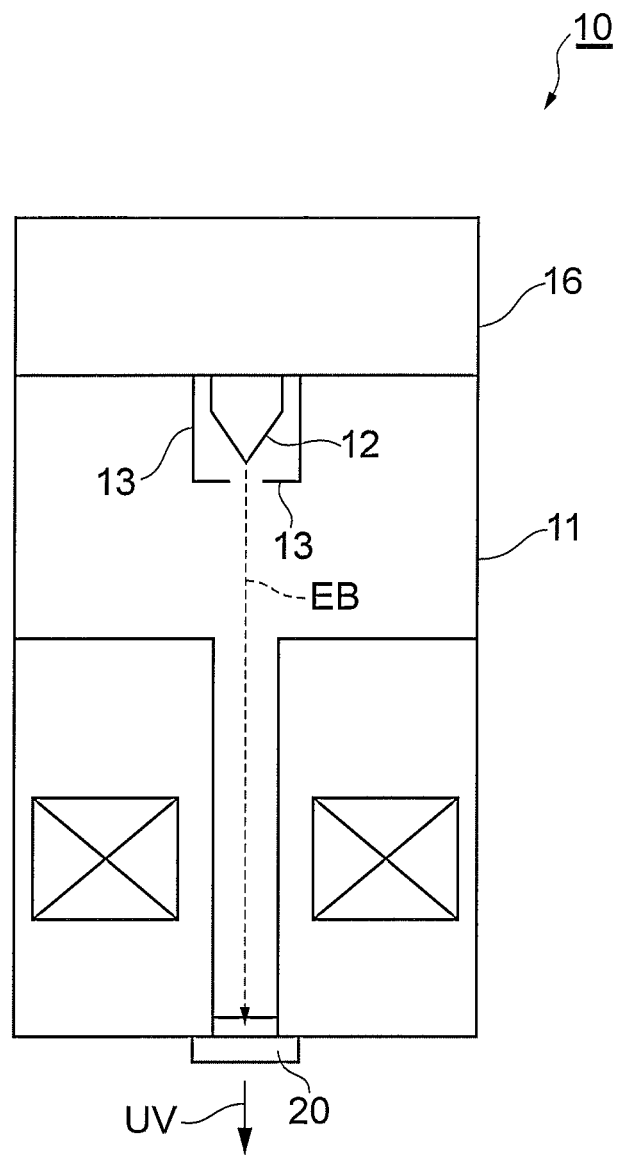
FIG. 1 is a schematic diagram illustrating an internal configuration of an electron-beam-excited ultraviolet light source according to an embodiment.

FIG. 1 is a schematic diagram illustrating an internal configuration of an electron-beam-excited ultraviolet light source 10 according to the present embodiment. As illustrated in FIG. 1, in the present electron-beam-excited ultraviolet light source 10, an electron source 12 and an extraction electrode 13 are arranged at the upper end side inside the vacuum-pumped glass container (electron tube) 11. Then, when an appropriate extraction voltage is applied from a power supply unit 16 between the electron source 12 and the extraction electrode 13, an electron beam EB that is accelerated by a high voltage is emitted from the electron source 12. An electron source (for example, a cold cathode such as carbon nanotubes, or a hot cathode) that emits an electron beam having a large area, for example, can be used as the electron source 12.

An ultraviolet light generating target 20 is arranged at the lower end side inside the container 11. The ultraviolet light generating target 20, for example, is set to the ground potential, and a high negative voltage is applied from the power supply unit 16 to the electron source 12. Accordingly, the electron beam EB emitted from the electron source 12 enters, with irradiation, the ultraviolet light generating target 20. The ultraviolet light generating target 20 is excited upon receiving the electron beam EB and generates ultraviolet light UV.

Figure 2:
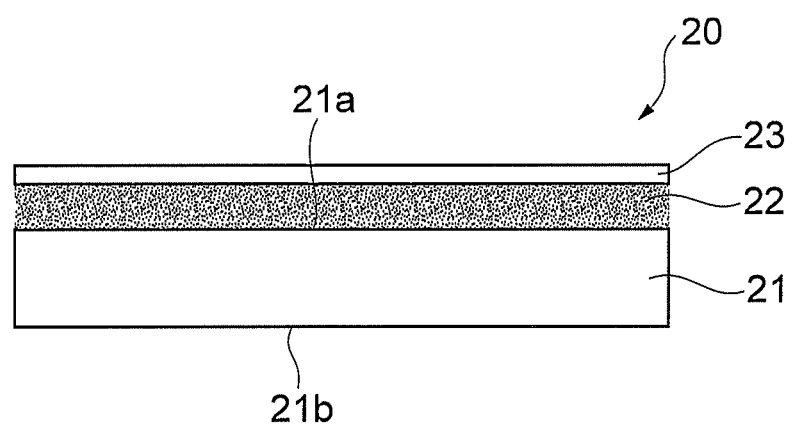
FIG. 2 is a side view illustrating a configuration of an ultraviolet light generating target.

FIG. 2 is a side view illustrating a configuration of the ultraviolet light generating target 20. As illustrated in FIG. 2, the ultraviolet light generating target 20 includes a substrate 21, a light-emitting layer 22 provided on the substrate 21, and an aluminum film 23 provided on the light-emitting layer 22. The substrate 21 is a plate-like member made of sapphire ($Al_2O_3$), quartz, ($SiO_2$), or rock crystal, which allows ultraviolet light (wavelength of 400 nm or less) to penetrate, and has a main surface 21$a$ and a back surface 21$b$. A favorable thickness of the substrate 21 is 0.1 mm or more and 10 mm or less.

The light-emitting layer 22 is excited upon receiving the electron beam EB shown in FIG. 1 and generates the ultraviolet light UV. The light-emitting layer 22 includes powdered or granular Pr:LuAG crystals. Here, the Pr:LuAG crystals may be either one of Pr:LuAG single crystals and Pr:LuAG polycrystals, or a mixture of both. As can be seen from the examples described later, the favorable thickness of the light-emitting layer 22 is 0.5 μm or more and 30 μm or less. Also, the favorable median diameter of the light-emitting layer 22 is 0.5 μm or more and 30 μm or less. Furthermore, the Pr concentration of the Pr:LuAG crystals is preferably 0.05 atom % or more and 2.0 atom % or less, and more preferably, 0.1 atom % or more and 1.0 atom % or less.

The effect obtained by the present embodiment will be described. As can be seen from each example described later, by using powdered or granular Pr:LuAG crystals as an ultraviolet light generating target, the ultraviolet light generating efficiency can be improved more remarkably than when a Pr:LuAG single crystal is used. The ultraviolet light generating target 20 of the present embodiment includes the light-emitting layer 22 containing powdered or granular Pr:LuAG crystals, and therefore, the ultraviolet light can be generated with high efficiency. Such an action is considered to be based on the fact that by converting Pr:LuAG crystals to a powdered or granular form, the reaction area between the Pr:LuAG crystals and the electron beam increases and the light extraction efficiency also increases.

Furthermore, because the light-emitting layer of the present embodiment is formed by a method of, for example, depositing powdered or granular Pr:LuAG crystals on a substrate, an ultraviolet light generating target having a large area can be produced with ease.

First Example

Next, a first example of the above-described embodiment will be described. In the present example, first, a synthetic quartz substrate having a diameter of 18.6 mm and a thickness of 1.2 mm was prepared. Next, by preparing a Pr:LuAG single crystal substrate and then grinding the Pr:LuAG single crystal substrate using a mortar, powdered or granular Pr:LuAG single crystals were formed. Subsequently, the light-emitting layer was formed by depositing the powdered or granular Pr:LuAG single crystals on the synthetic quartz substrate by sedimentation method. Then, an organic film (nitrocellulose) was formed on the light-emitting layer, and an aluminum film was deposited on the organic film by evaporation. Finally, the powdered or granular Pr:LuAG single crystals were integrated by baking the light-emitting layer. The thickness of the light-emitting layer after baking was 10 μm.

Figure 3:
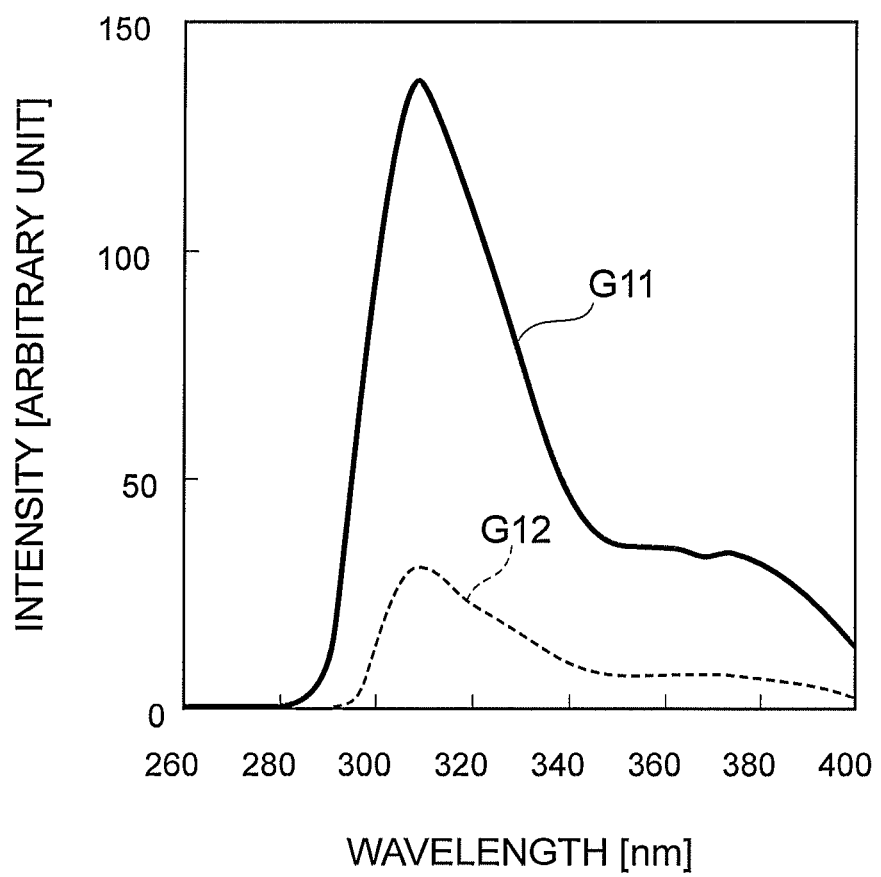
FIG. 3 is a graph illustrating a spectrum of the ultraviolet light obtained by irradiating the ultraviolet light generating target formed by a first example with an electron beam.
Figure 4:
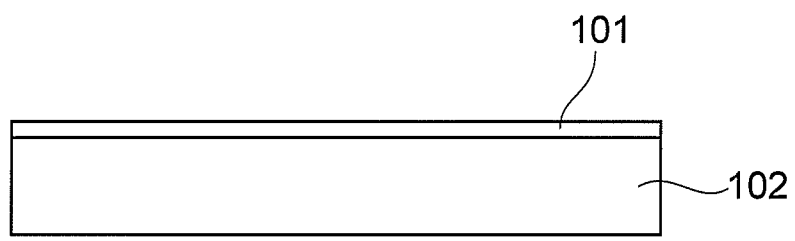
FIG. 4 is a diagram illustrating a Pr:LuAG single crystal substrate with an aluminum film deposited on the surface.

A graph G11 of FIG. 3 illustrates a spectrum of the ultraviolet light obtained by irradiating the ultraviolet light generating target formed by the present example with an electron beam. In FIG. 3, a graph G12 is shown together for comparison. As illustrated in FIG. 4, the graph G12 is a spectrum of the ultraviolet light obtained by irradiating a Pr:LuAG single crystal substrate 102 where an aluminum film 101 is deposited on the surface by evaporation, with an electron beam. In the graph G11 and G12, the accelerating voltage of the electron beam was set to 10 kV, the intensity of the electron beam (amount of electric current) was set to 50 μA, and the diameter of the electron beam was set to 2 mm. As can be seen from FIG. 3, as compared to the Pr:LuAG single crystal substrate, in the light-emitting layer of the present embodiment, which contains powdered or granular Pr:LuAG single crystals, the peak intensity of the ultraviolet light generated through irradiation with an electron beam becomes significantly higher (that is, the luminous efficiency becomes significantly higher).

Second Example

Next, a second example of the above-described embodiment will be described. In the present example, in order to investigate the effect of the substrate material of the ultraviolet light generating target, a synthetic quartz substrate and a sapphire substrate were prepared. As for the synthetic quartz substrate, a substrate having a diameter of 18.6 mm and a thickness of 1.2 mm was prepared. In addition, as for the sapphire substrate, a substrate having a diameter of 18 mm and a thickness of 0.43 mm was prepared. Then, a light-emitting layer containing powdered or granular Pr:LuAG single crystals and an aluminum film were formed on the above substrates using the same method as in the first embodiment.

Figure 5:
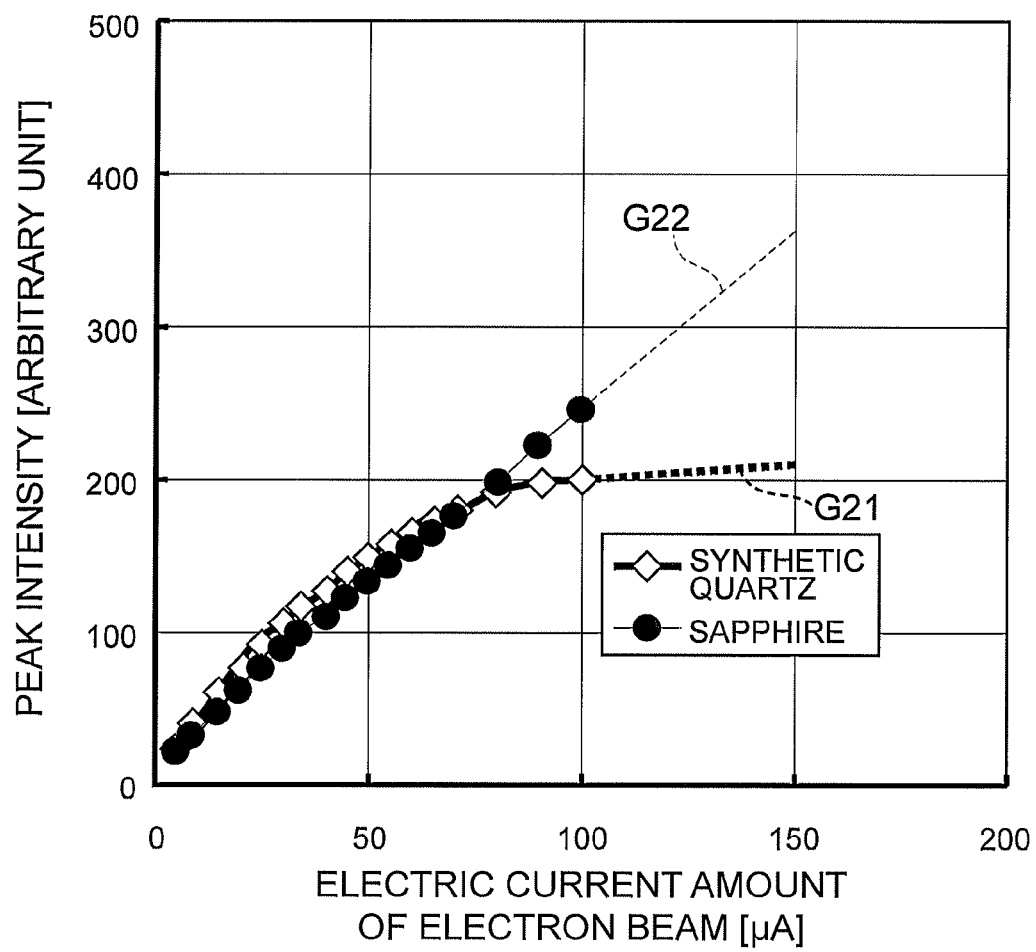
FIG. 5 is a graph illustrating a relationship between the amount of electric current and the peak intensity of the ultraviolet light when the light-emitting layer formed on each substrate is irradiated with an electron beam, in a second example.

FIG. 5 is a graph illustrating a relationship between the amount of electric current and the peak intensity of the ultraviolet light when the light-emitting layer formed on each substrate is irradiated with an electron beam. In FIG. 5, a graph G21 is a graph concerning the light-emitting layer formed on the synthetic quartz substrate. A graph G22 is a graph concerning the light-emitting layer formed on the sapphire substrate. As illustrated in FIG. 5, with regard to the light-emitting layer formed on the synthetic quartz substrate, when the amount of electric current increases, the rate of increase of the emission intensity declines. In contrast, the light-emitting layer formed on the sapphire substrate showed excellent linearity in that the rate of increase did not decline even when the amount of electric current increased. It is considered that such a result is obtained due to the fact that as compared to the synthetic quartz substrate, the thermal conductivity of the sapphire substrate is better.

Third Example

Figure 6:
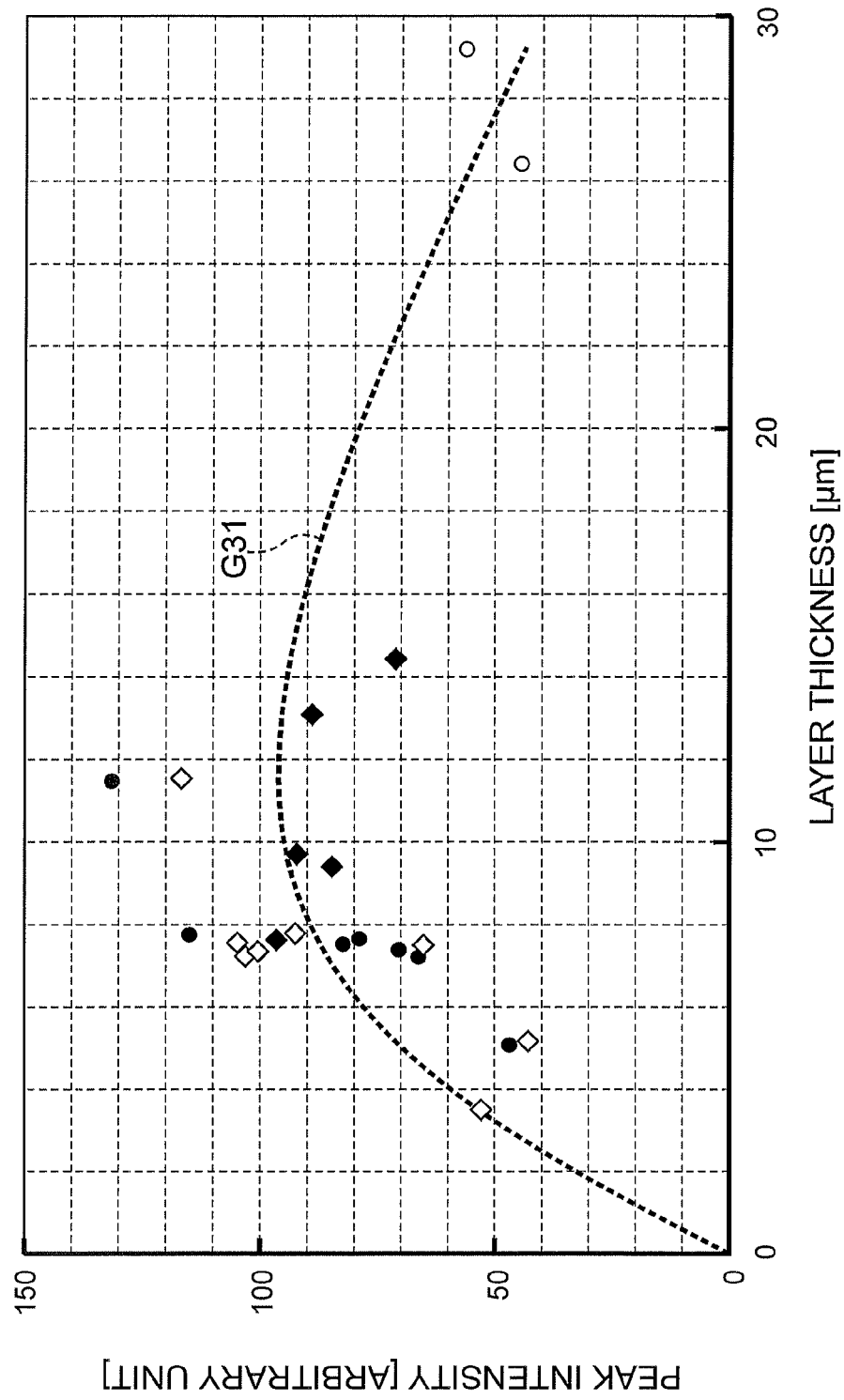
FIG. 6 is a graph illustrating a relationship between the thickness of the light-emitting layer and the peak intensity of the ultraviolet light in a third example.

Next, a third example of the above-described embodiment will be described. In the present example, an ultraviolet light generating target was formed by the same method as in the first example, and an experiment was performed regarding the relationship between the thickness of the light-emitting layer and the peak intensity of the ultraviolet light. That is, light-emitting layers were formed by depositing powdered or granular Pr:LuAG crystals in various thicknesses, and after measuring the peak intensity of the ultraviolet light generated by irradiating the light-emitting layers with an electron beam, the thickness was measured by observing the cross section of the light-emitting layers by using a SEM. FIG. 6 shows the results of the above in the form of a graph illustrating the relationship between the thickness of the light-emitting layers and the peak intensity of the ultraviolet light. A G31 curve in the figure is an approximated curve. Also, in FIG. 6, the accelerating voltage of the electron beam was set to 10 kV, the intensity of the electron beam (amount of electric current) was set to 50 μA, and the diameter of the electron beam was set to 2 mm.

With reference to FIG. 6, when the thickness of the light-emitting layer falls below a certain value (approximately 12 μm), then the peak intensity of the ultraviolet light increases as the light-emitting layer thickens, and the luminous efficiency improves. However, if the thickness of the light-emitting layer exceeds this value, the peak intensity of the ultraviolet light starts falling, in contrast. It is understood from the graph that in order to obtain a sufficiently practical ultraviolet light intensity (luminous efficiency), the thickness of the light-emitting layer is preferably 0.5 μm or more and 30 μm or less, and more preferably 6 μm or more and 20 μm or less.

Fourth Example

Figure 7:
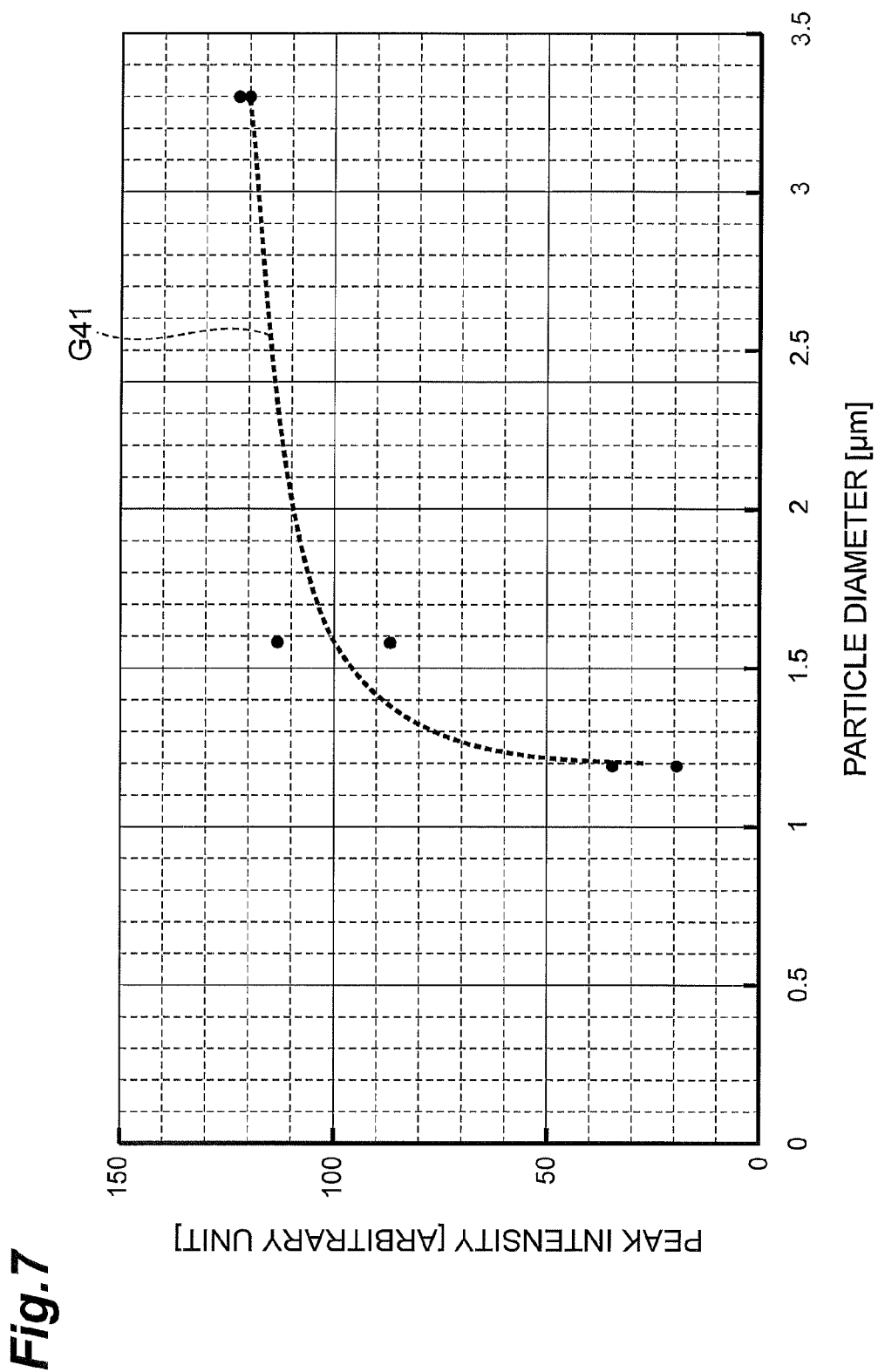
FIG. 7 is a graph illustrating a relationship between the median diameter of the Pr:LuAG crystals and the peak intensity of the ultraviolet light in a fourth example.

Subsequently, an explanation of a fourth example of the above-described embodiment will be provided. In this example, an experiment was conducted regarding the relationship between the median diameter of the powdered or granular Pr:LuAG crystals included in the light-emitting layer and the peak intensity of the ultraviolet light. That is, light-emitting layers were formed on a plurality of substrates by depositing powdered or granular Pr:LuAG crystals, and the peak intensity of the ultraviolet light generated by irradiating the light-emitting layers with an electron beam was measured. The median diameter of the Pr:LuAG crystals included in the light-emitting layers was measured using a particle size distribution analyzer before being deposited on the substrate. FIG. 7 shows the results of the above in the form of a graph illustrating the relationship between the median diameter of the Pr:LuAG crystals and the peak intensity of the ultraviolet light. A G41 curve in the figure is an approximated curve. In FIG. 7, the accelerating voltage of the electron beam was set to 10 kV, the intensity of the electron beam (amount of electric current) was set to 70 μA, and the diameter of the electron beam was set to 2 mm.

With reference to FIG. 7, the larger the median diameter of the Pr:LuAG crystals, the higher the peak intensity of the ultraviolet light, and the luminous efficiency improves. It must be noted when the median diameter of the Pr:LuAG crystals exceeds 1.6 μm, the rate of increase in the peak intensity of the ultraviolet light is reduced. Also, it is understood from the graph that if the median diameter of the Pr:LuAG crystals is 0.5 μm or more, a sufficiently practical ultraviolet light intensity (luminous efficiency) can be obtained. If the median diameter of the Pr:LuAG crystals is less than 0.5 μm, the luminous efficiency is considered to be reduced due to the following reasons (1) through (3). (1) Although the light emitted by the light-emitting layer is scattered by the Pr:LuAG crystal grains, if the median diameter of the Pr:LuAG crystals is less than 0.5 μm, the scattering by the crystal grains increases, and therefore, the ratio of light that is output after passing through the light-emitting layer declines. (2) Because the defect density is higher near the surface of the Pr:LuAG crystal grains as compared to the inside of the particles, the luminous efficiency near the surface of the particles is lower as compared to the luminous efficiency of the inside of the particles. Thus, if the total volume of the Pr:LuAG crystals is constant, then, the smaller the particle diameter of the Pr:LuAG crystal grains, the larger the surface area of the Pr:LuAG crystals. Therefore, if the median diameter of the Pr:LuAG crystals is less than 0.5 μm, the ratio of the portion where the defect density is high and the luminous efficiency is low increases, and the luminous efficiency declines. (3) If the median diameter of the Pr:LuAG crystals is less than 0.5 μm, the heat dissipation efficiency during irradiation of the electron beam is low, and therefore, the temperature of the Pr:LuAG crystals rises and the luminous efficiency declines.

The median diameter of the Pr:LuAG crystals is preferably 30 μm or less. When the median diameter of the Pr:LuAG crystals is 30 μm or less, the peeling of the Pr:LuAG crystals from the substrate can be suppressed when Pr:LuAG crystals are deposited on the substrate.

Fifth Example

Next, a fifth example of the above-described embodiment will be described. In the present example, first, a polycrystalline plate containing 0.7 atom % of Pr was formed. Next, by grinding the polycrystalline plate by using a mortar, a powdered or granular Pr:LuAG polycrystal was formed. Following this, a light-emitting layer was formed by depositing the powdered or granular Pr:LuAG polycrystals on a synthetic quartz substrate by sedimentation method. Then, an organic film (nitrocellulose) was formed on the light-emitting layer, and an aluminum film was deposited on the organic film by evaporation. Finally, by baking the light-emitting layer, the powdered or granular Pr:LuAG polycrystals were integrated. The thickness of the light-emitting layer after baking was 10 μm.

Figure 8:
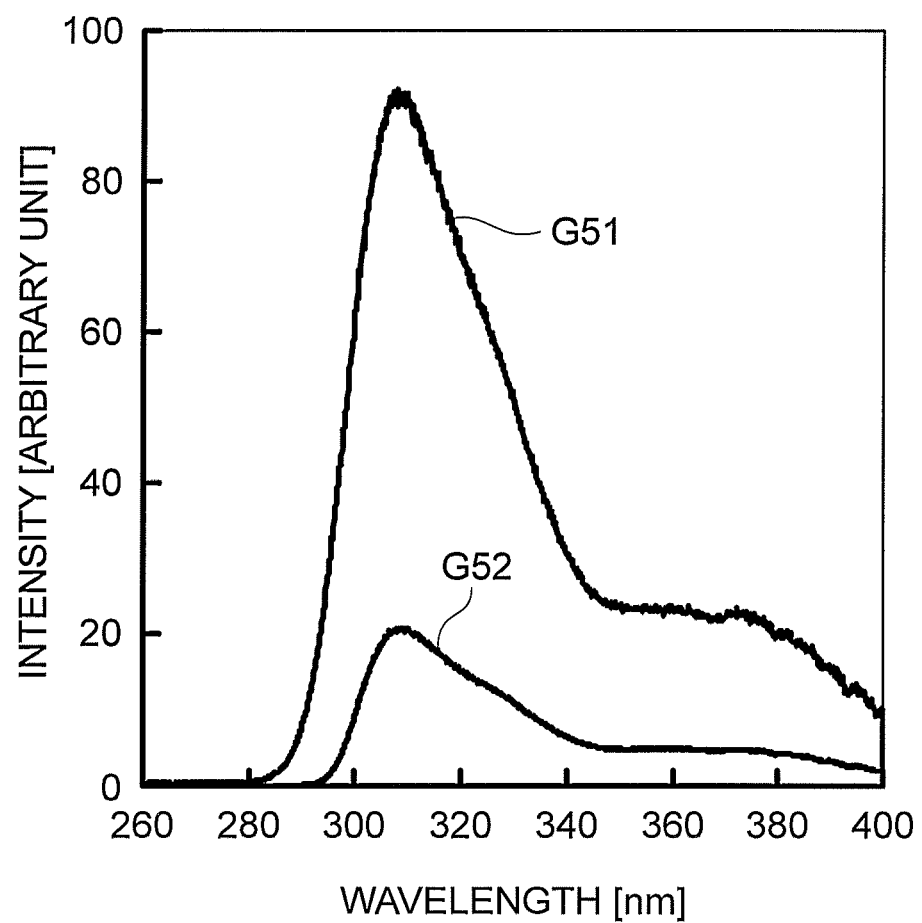
FIG. 8 is a graph illustrating a spectrum of the ultraviolet light obtained by irradiating the ultraviolet light generating target formed by a fifth example with an electron beam.

A graph G51 in FIG. 8 illustrates a spectrum of the ultraviolet light obtained by irradiating the ultraviolet light generating target formed by the present example with an electron beam. In FIG. 8, a graph G52 is shown together for comparison. The graph G52 is a spectrum of ultraviolet light obtained by irradiating an electron beam on a Pr:LuAG polycrystalline plate where an aluminum film is deposited on the surface by evaporation. With reference to FIG. 8, as compared to the Pr:LuAG polycrystalline plate, in the light-emitting layer of the present embodiment, which contains powdered or granular Pr:LuAG polycrystals, the peak intensity of the ultraviolet light generated upon irradiation with an electron beam becomes significantly higher (that is, the luminous efficiency becomes significantly higher).

Sixth Example

Next, a sixth example of the above-described embodiment will be described. In the present example, when the median diameter of the powdered or granular Pr:LuAG crystals included in the light-emitting layer has various values, an experiment was conducted regarding the relationship between the thickness of the light-emitting layer and the peak intensity of the ultraviolet light. That is, through each of the Pr:LuAG crystals having a median diameter of 0.5 μm, 1.0 μm, 6.5 μm and 30 μm were deposited to form a plurality of light-emitting layers having a different thickness for each median diameter, the peak intensities of the ultraviolet lights generated by irradiating the light-emitting layers with an electron beam were measured. The median diameters of the Pr:LuAG crystals included in the light-emitting layers were measured using a particle size distribution analyzer before being deposited on the substrate.

Figure 9:
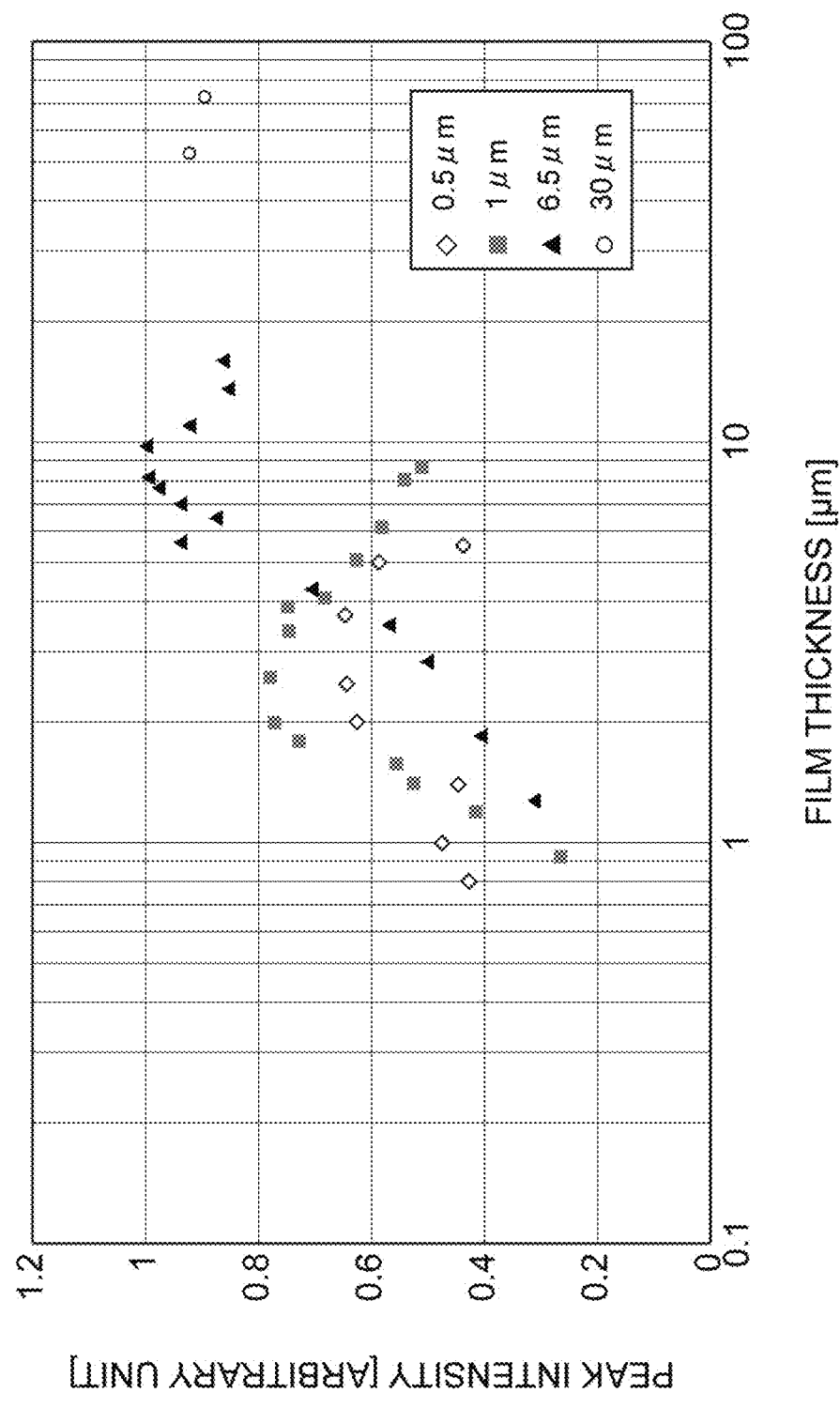
FIG. 9 is a graph showing plotting of measurement results on a graph in which the vertical axis indicates the peak intensity and the horizontal axis indicates the thickness of the light-emitting layer (logarithmic scale).
Figure 10:
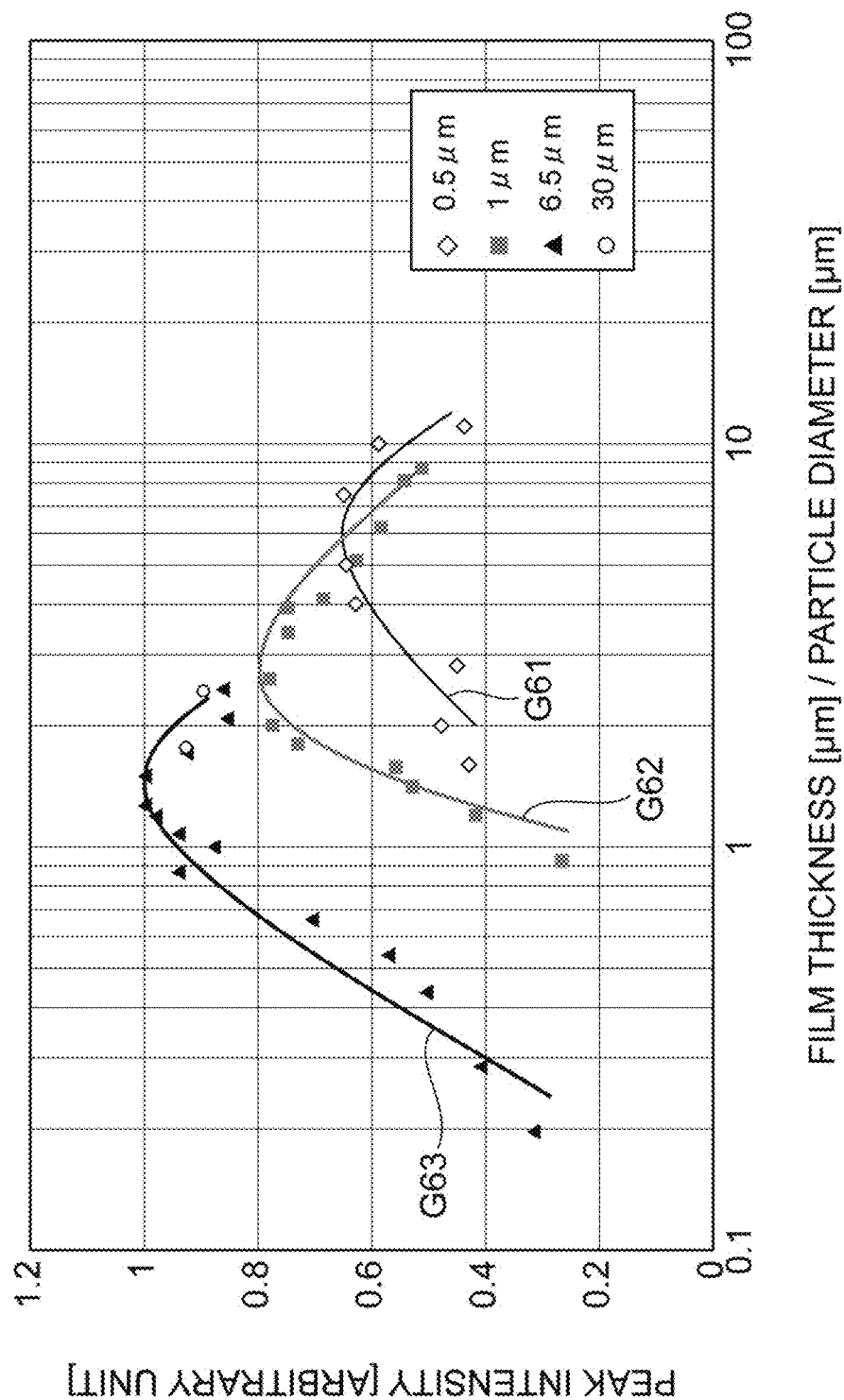
FIG. 10 is a graph in which the value obtained by dividing the film thickness with the median diameter is expressed on the horizontal axis (logarithmic scale).
Figure 11:
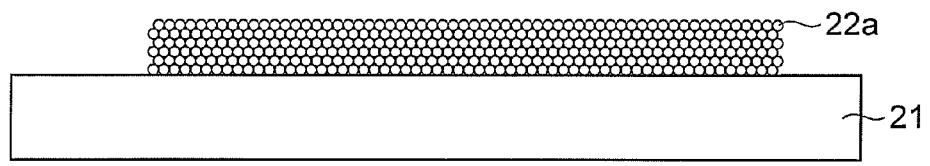
FIG. 11 is a diagram that schematically illustrates the Pr:LuAG crystal grains deposited on the substrate.
Figure 11:
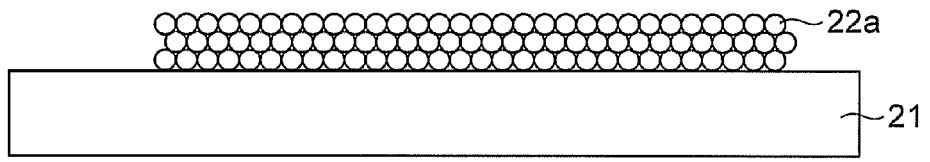
Figure 11:
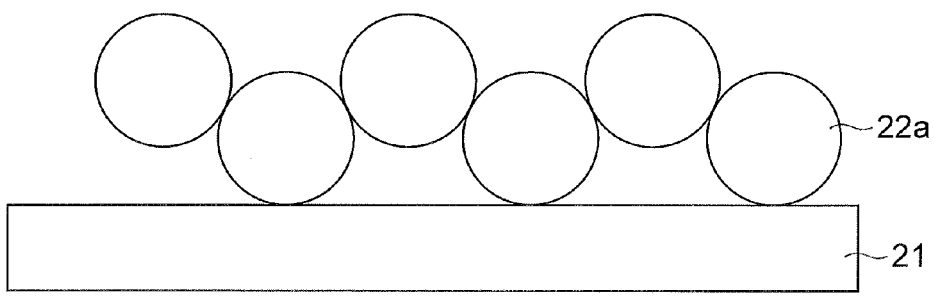

FIG. 9 is a graph showing plotting of results on a graph in which the vertical axis indicates the peak intensity and the horizontal axis indicates the thickness of the light-emitting layer (logarithmic scale). FIG. 10 is a graph in which the value obtained by dividing the film thickness with the median diameter (that is, the number of laminates of the Pr:LuAG crystal grains) is expressed on the horizontal axis (logarithmic scale). Curves G61, G62 and G63 in the figure are approximate curves for each of the median diameters of 0.5 μm, 1.0 μm and 6.5 μm. FIG. 11(a) through 11(c) schematically illustrate Pr:LuAG crystal grains 22a deposited on the substrate 21.

With reference to FIG. 9 and FIG. 10, the thickness in which the peak intensity increases (that is, the luminous efficiency improves) differs depending on the median diameter of the Pr:LuAG crystals. That is, when the median diameter of the Pr:LuAG crystals is 0.5 μm, the thickness at which the peak intensity of the ultraviolet light becomes the highest is 3 μm, and the number of laminates in this case is six (FIG. 11(a)). And, the range of thickness at which a sufficiently practical peak intensity can be obtained is 0.5 μm or more and 5 μm or less. Furthermore, when the median diameter of the Pr:LuAG crystals is 1.0 the thickness at which the peak intensity of the ultraviolet light becomes the highest is 3 μm, and the number of laminates in this case is three (FIG. 11(b)). And, the range of thickness at which a sufficiently practical peak intensity can be obtained is 1 μm or more and 10 μm or less. Furthermore, when the median diameter of the Pr:LuAG crystals is 6.5 μm, the thickness at which the peak intensity of the ultraviolet light becomes the highest is 10 μm, and the number of laminates in this case is approximately 1.5 (FIG. 11(c)). And, the range of thickness at which a sufficiently practical peak intensity can be obtained is 3 μm or more and 30 μm or less.

As described above, the smaller the median diameter of the Pr:LuAG crystals, the more significant the decline in the luminous efficiency when the light-emitting layer becomes thicker. This is due to the fact that the higher the number of laminates of the Pr:LuAG crystal grains, the lesser the transmittance of the ultraviolet light in the light-emitting layer. Furthermore, for all the median diameters, if the thickness of the light-emitting layer becomes thinner than a particular value, the luminous efficiency declines. This is considered to be due to the fact that if the thickness of the light-emitting layer becomes thinner, the coverage of the substrate surface by the Pr:LuAG crystals lowers. For all median diameters, the coverage at the highest peak intensity of the ultraviolet light is 100%.

Figure 12:
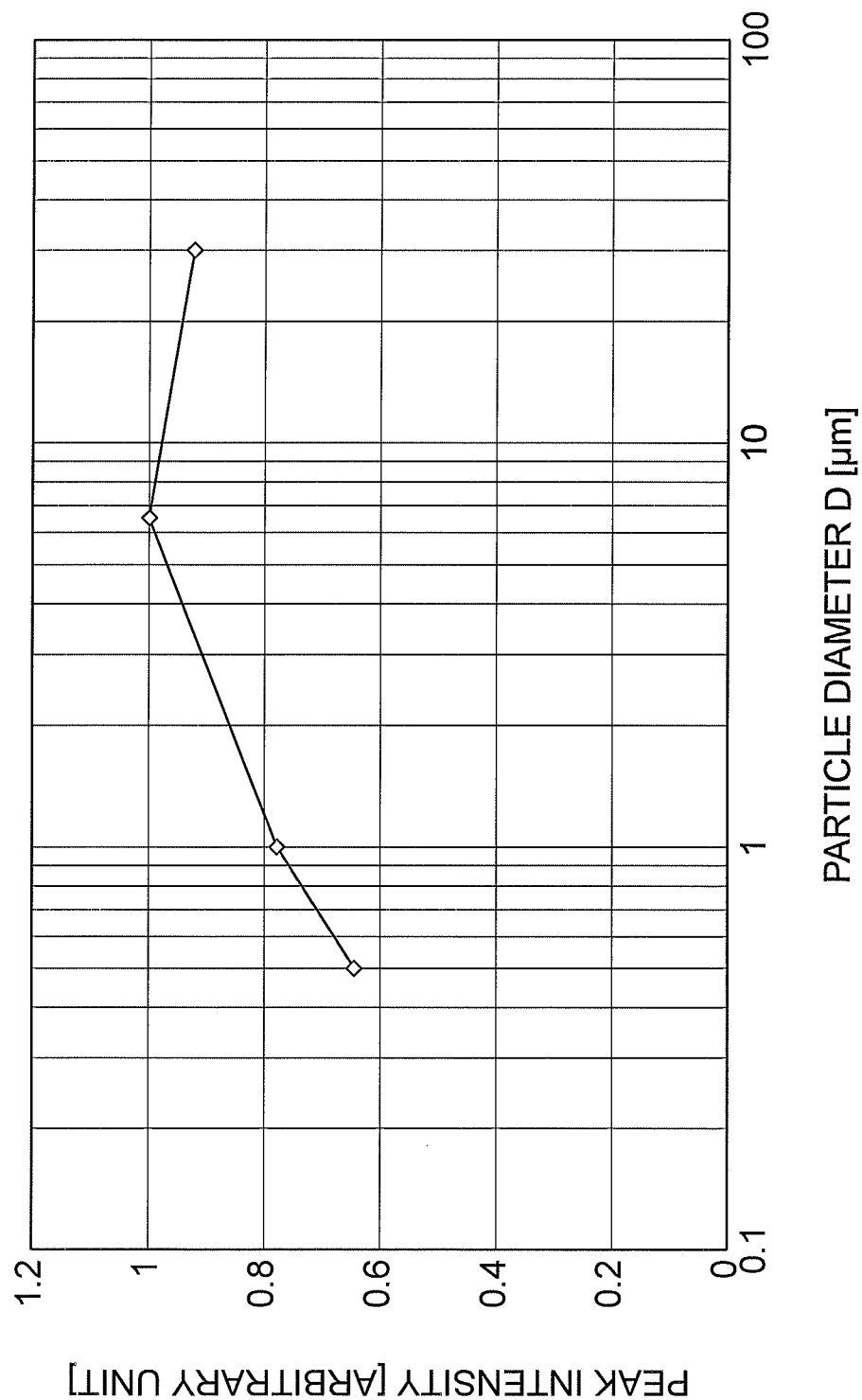
FIG. 12 is a graph illustrating a relationship between the median diameter of the Pr:LuAG crystals in the present example and the peak intensity of the ultraviolet light.

FIG. 12 is a graph illustrating a relationship between the median diameter of the Pr:LuAG crystals in the present example and the peak intensity of the ultraviolet light. With reference to FIG. 12, when the median diameter of the Pr:LuAG crystals falls below 6.5 μm, the larger the median diameter, the higher the peak intensity of the ultraviolet light becomes, and the luminous efficiency improves. However, if the median diameter exceeds 6.5 μm, the peak intensity of the ultraviolet light starts falling, in contrast. It is understood from the graph that in order to improve the luminous efficiency of the ultraviolet light, the favorable range of the median diameter of the Pr:LuAG crystals is 0.5 μm or more and 100 μm or less. It must be noted that if the median diameter exceeds 30 μm, adhesion between the particles of the Pr:LuAG crystals and the substrate is weakened and peeling occurs, and thus, the favorable range of the practical median diameter is 0.5 μm or more and 30 μm or less.

Seventh Example

Next, a fifth example of the above-described embodiment will be described. In the present example, the formation of a light-emitting layer with using a binder, and the formation of a light-emitting layer by heat treatment, without using a binder are explained.

<Formation of a Light-Emitting Layer with Using a Binder>

First, a sapphire substrate with a diameter of 12 mm and a thickness of 2 mm was prepared. Next, by preparing a Pr:LuAG single crystal substrate and then grinding the Pr:LuAG single crystal substrate using a mortar, powdered or granular Pr:LuAG single crystals were formed.

Then, powdered or granular Pr:LuAG single crystals, pure water, an aqueous solution of potassium silicate ($K_2SiO_3$) and an aqueous solution of barium acetate as the binder material were mixed. The liquid mixture was applied on the sapphire substrate, and Pr:LuAG single crystals and the binder material were deposited on the sapphire substrate by sedimentation method, thereby forming a light-emitting layer. Then, an organic film (nitrocellulose) was formed on the light-emitting layer, and an aluminum film was formed on the organic film by vacuum evaporation. Finally, by baking the light-emitting layer at 350° C. in the air, the organic film was decomposed and vaporized to obtain a structure in which the aluminum film was in contact with the light-emitting layer.

<Formation of a Light-Emitting Layer Through Heat Treatment>

First, a sapphire substrate with a diameter of 12 mm and a thickness of 2 mm was prepared. Next, by preparing a Pr:LuAG single crystal substrate and then grinding the Pr:LuAG single crystal substrate using a mortar, powdered or granular Pr:LuAG single crystals were formed.

Then, powdered or granular Pr:LuAG single crystals and a solvent (ethanol) were mixed, and after applying the liquid mixture on the sapphire substrate, the solvent was dried. In this way, a light-emitting layer was formed by depositing the Pr:LuAG single crystals on the sapphire substrate. Following this, heat treatment (at 1600° C.) of the light-emitting layer was performed in an atmosphere with reduced pressure. The heat treatment was performed to melt the surface of the powdered or granular Pr:LuAG single crystals, and then form a structure by fusing the surfaces of the crystal grains with each other and the surface of the crystal grains with the sapphire substrate so as to improve the adhesion of the light-emitting layer. Then, an organic film (nitrocellulose) was formed on the light-emitting layer, and an aluminum film was formed on the organic film by vacuum evaporation. Finally, by baking the light-emitting layer at 350° C. in the air, the organic film was decomposed and vaporized to obtain a structure in which the aluminum film was in contact with the light-emitting layer.

Figure 13:
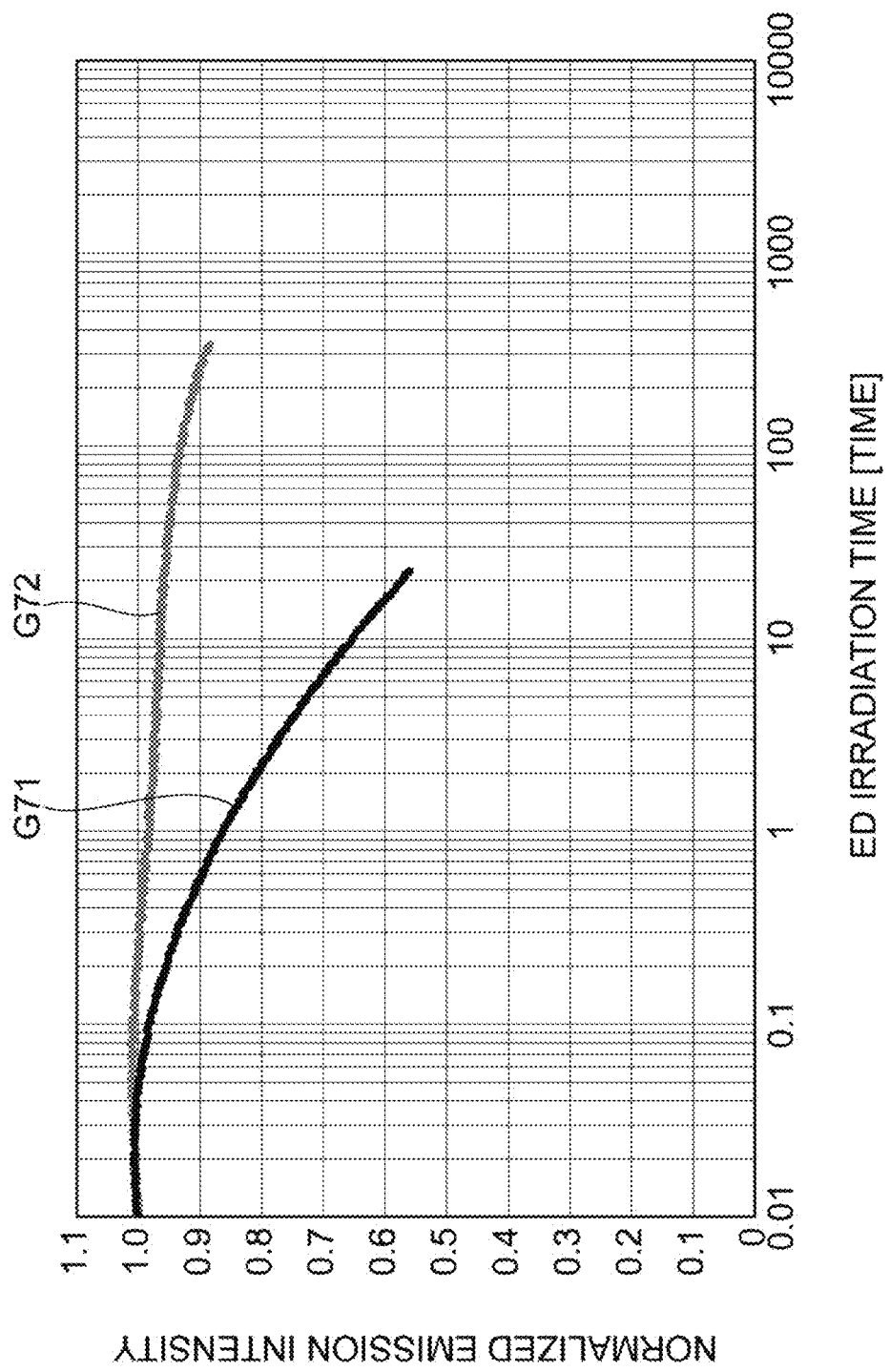
FIG. 13 is a graph illustrating the time-dependent changes in the emission intensity of the light-emitting layer formed by using a binder, and the emission intensity of the light-emitting layer formed by heat treatment.

FIG. 13 is a graph illustrating the time-dependent changes in the emission intensity of the light-emitting layer formed with using a binder, and the emission intensity of the light-emitting layer formed by heat treatment. In FIG. 13, the vertical axis represents the normalized emission intensity (the default value is 1.0), and the horizontal axis represents the irradiation time of the electron beam (unit: hours) on a logarithmic scale. A graph G71 illustrates the light-emitting layer formed with using a binder, and a graph G72 illustrates the light-emitting layer formed by heat treatment. In the graph G71 and the graph G72, the accelerating voltage of the electron beam was set to 10 kV, and the intensity of the electron beam (amount of electric current) was set to 200 μA.

As illustrated in FIG. 13, when the light-emitting layer was formed by heat treatment without using a binder (graph G72), the time-dependent changes in the emission intensity (decline in the emission intensity) were less as compared to the case when a binder was used (graph G71). This could possibly be due to the reasons described below. That is, in the case of formation of a light-emitting layer using a binder, in addition to the Pr:LuAG crystals, the binder material is also included in the finished light-emitting layer. When this light-emitting layer is irradiated with an electron beam having a strong energy, then, in addition to the ultraviolet light, an energy ray that is different from the ultraviolet light, for example, an X-ray is generated. And, when the energy ray passes through the substrate, the substrate is damaged. In case of using a binder, such a phenomenon occurs at each irradiation of the electron beam. Therefore, the damage is considered to be accumulated in the substrate, and the transmittance of ultraviolet light is considered to reduce gradually. It is also considered that, due to the degradation of the potassium and $SiO_2$ included in the binder, the luminous efficiency is declined.

In contrast, when a light-emitting layer is formed by heat treatment, the binder material is not included in the light-emitting layer, and therefore, generation of an energy ray different from the ultraviolet light is suppressed, and also, the degradation of the binder material does not occur. Therefore, the damage to the substrate is reduced, and the transmittance of ultraviolet light is considered to be maintained over a relatively long period of time. It must be noted that the damage caused by the energy ray that is different from the ultraviolet light is particularly remarkable in the sapphire substrate. Therefore, in the case of forming a light-emitting layer on a sapphire substrate, it is desirable to form a light-emitting layer by heat treatment.

Figure 14:
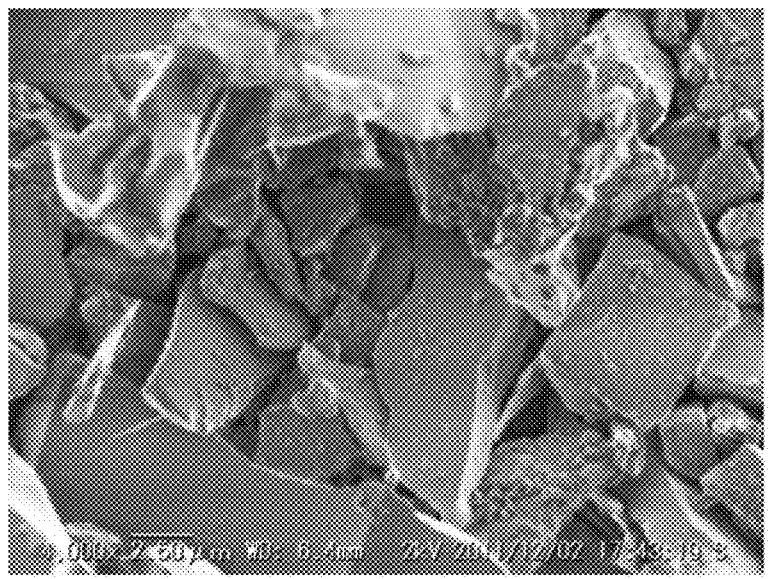
FIG. 14 is an electron microscope (SEM) photograph of the condition of Pr:LuAG crystal grains of the light-emitting layer.
Figure 14:
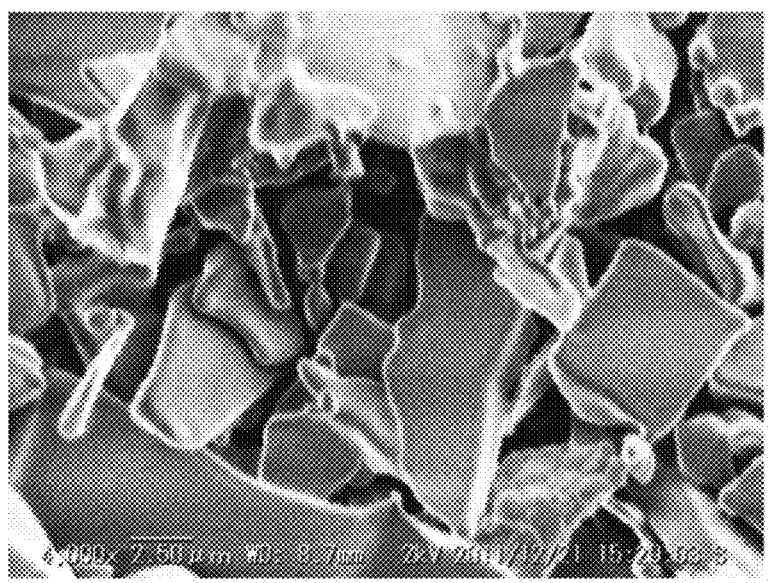
Figure 15:
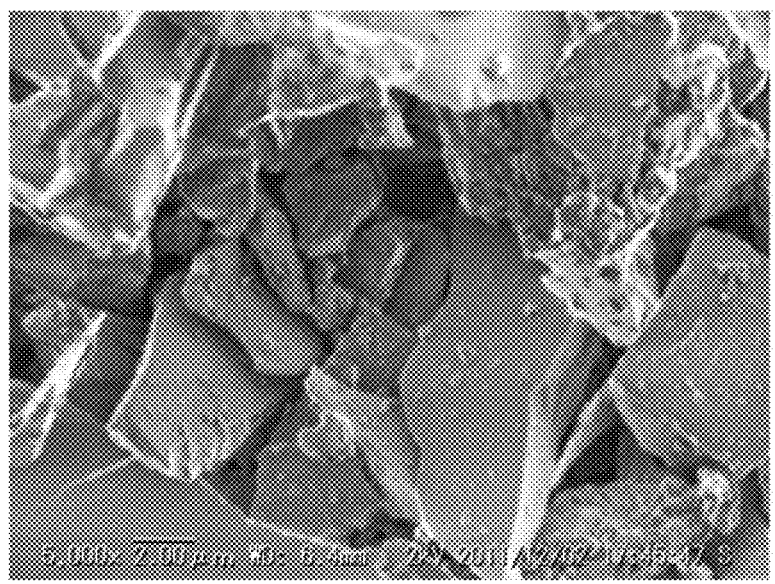
FIG. 15 is an enlarged photograph of FIG. 14.
Figure 15:
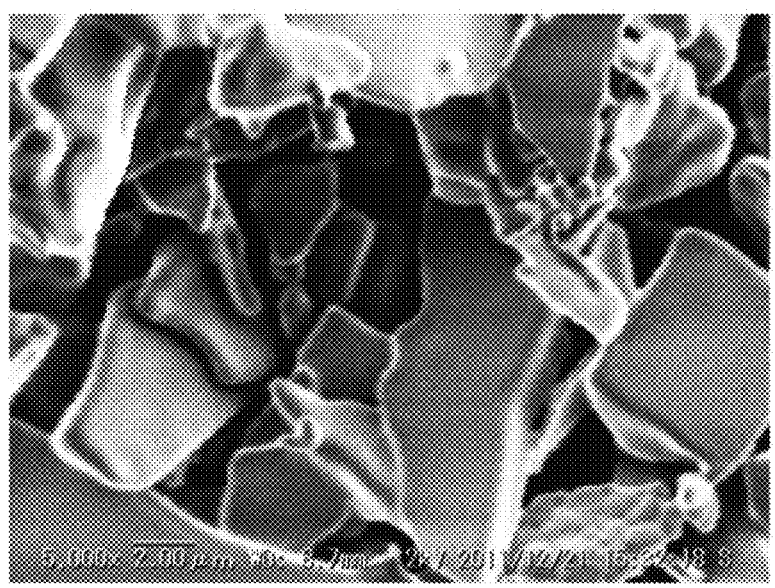
Figure 16:
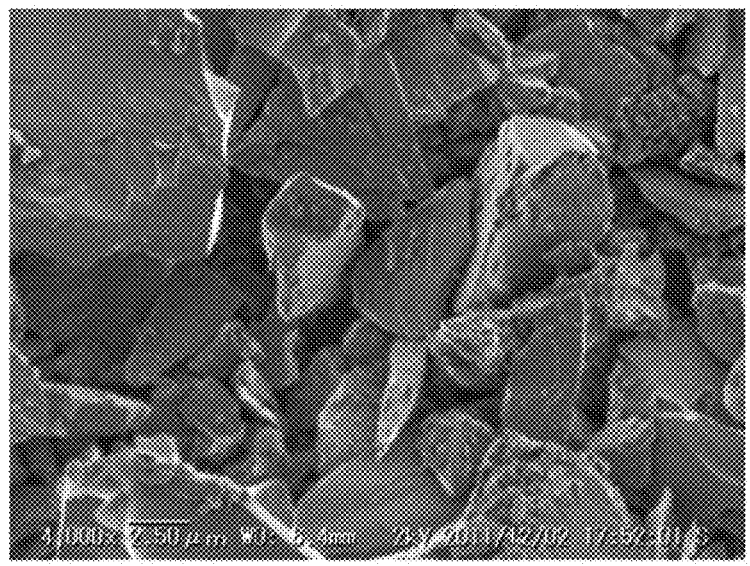
FIG. 16 is a SEM photograph of the condition of the Pr:LuAG crystal grains of the light-emitting layer.
Figure 16:
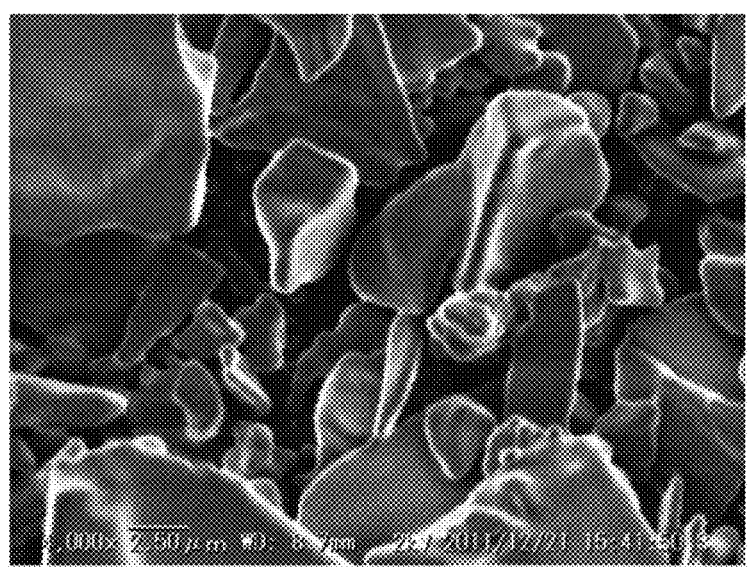
Figure 17:
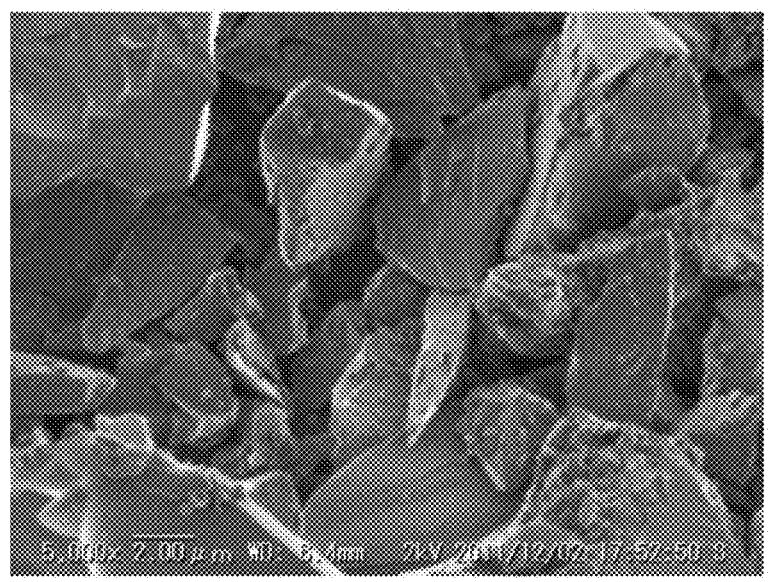
FIG. 17 is an enlarged photograph of FIG. 16.
Figure 17:
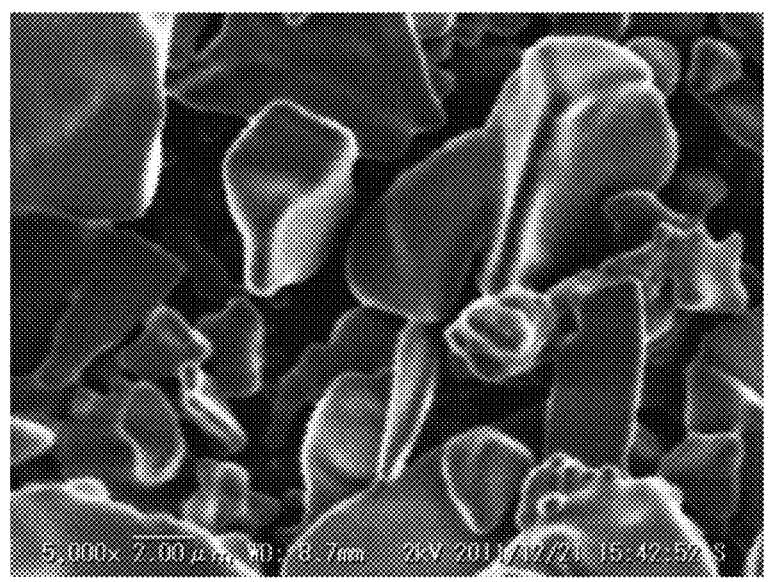
Figure 18:
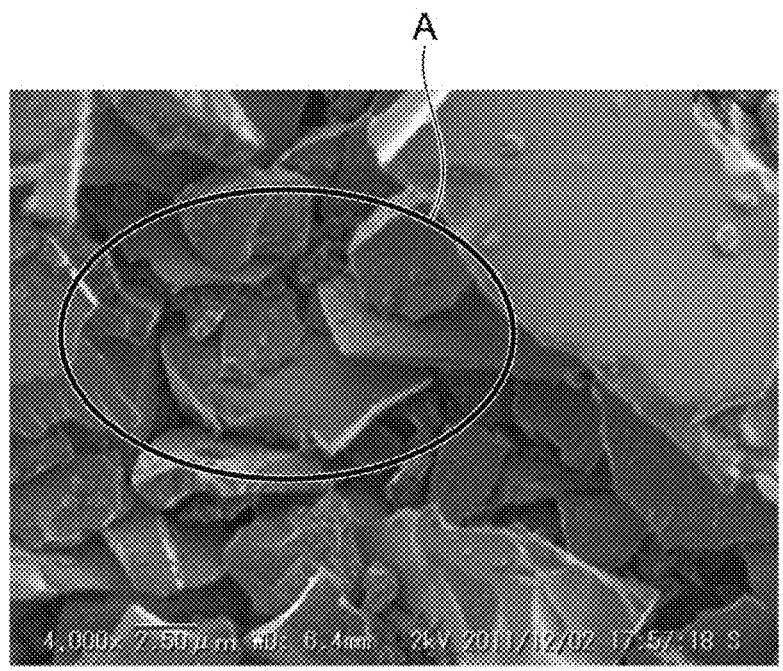
FIG. 18 is a SEM photograph of the condition of the Pr:LuAG crystal grains of the light-emitting layer.
Figure 18:
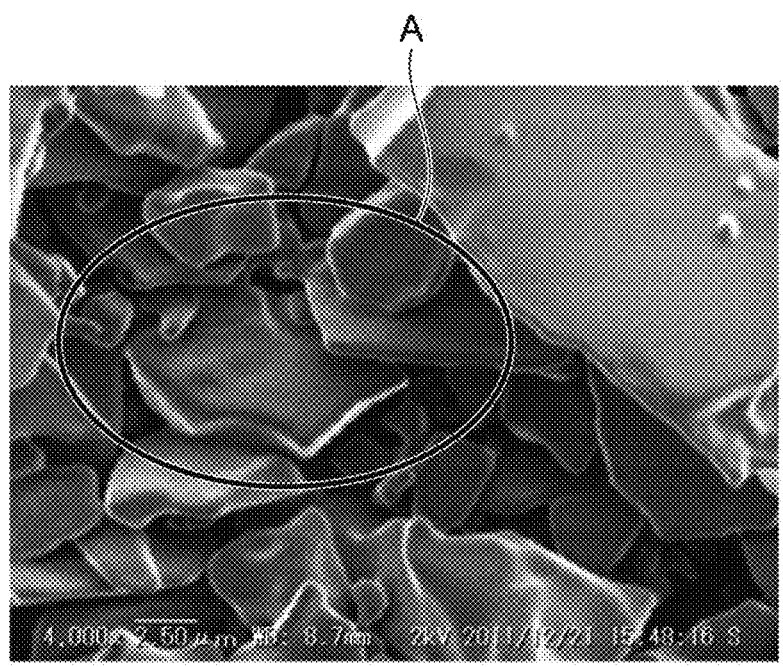
Figure 19:
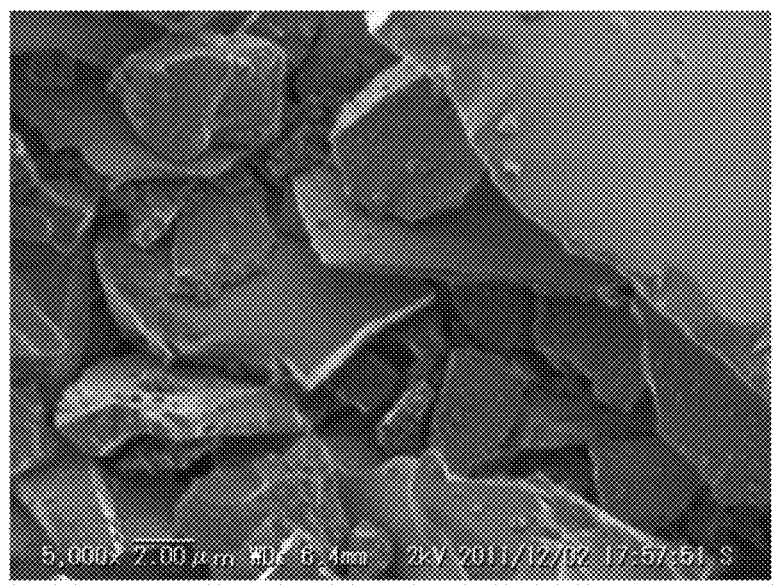
FIG. 19 is an enlarged photograph of FIG. 18.
Figure 19:
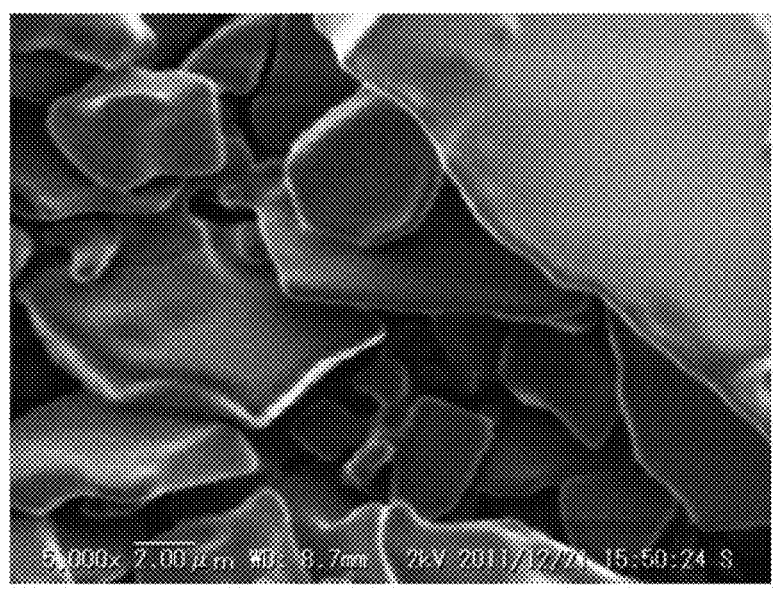
Figure 20:
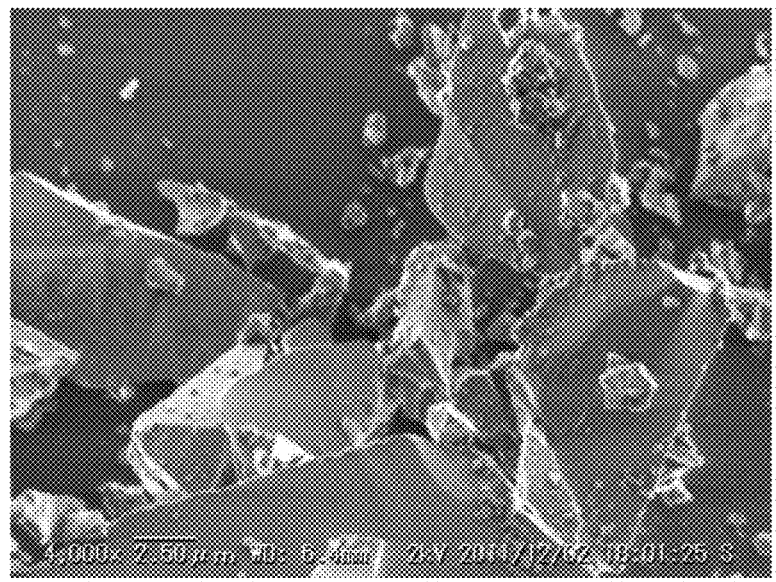
FIG. 20 is a SEM photograph of the condition of the Pr:LuAG crystal grains of the light-emitting layer.
Figure 20:
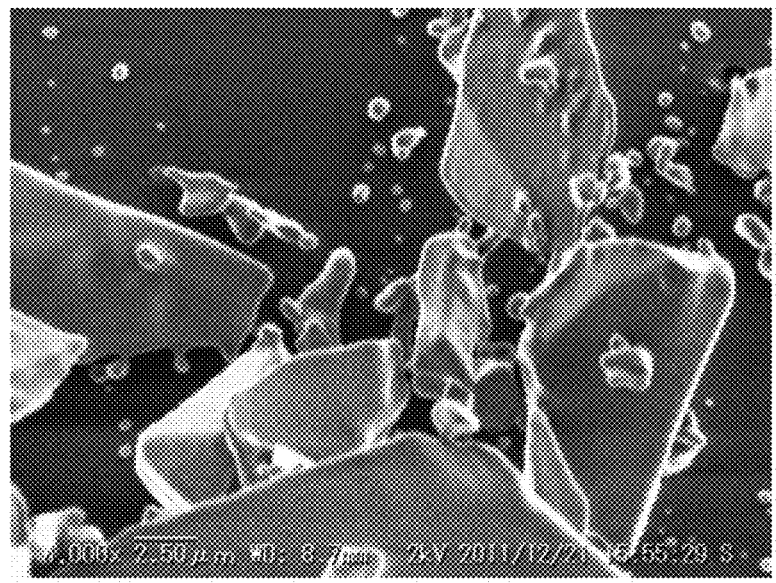
Figure 21:
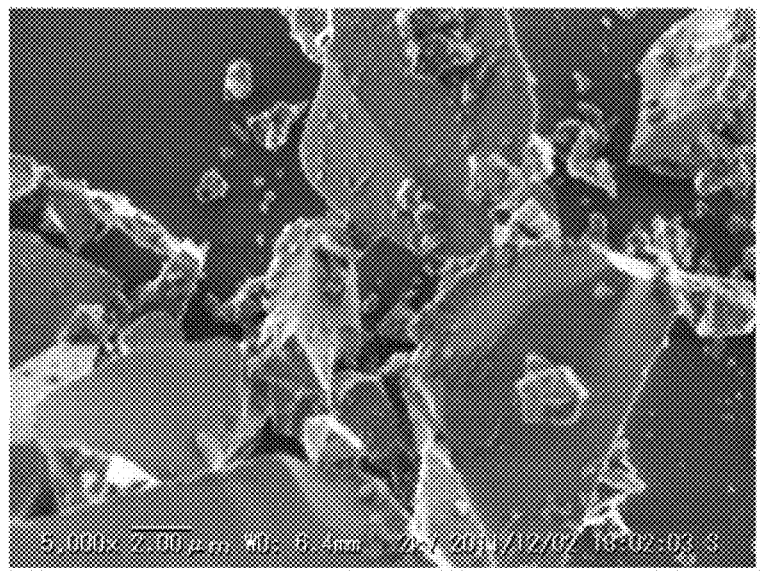
FIG. 21 is an enlarged photograph of FIG. 20.
Figure 21:
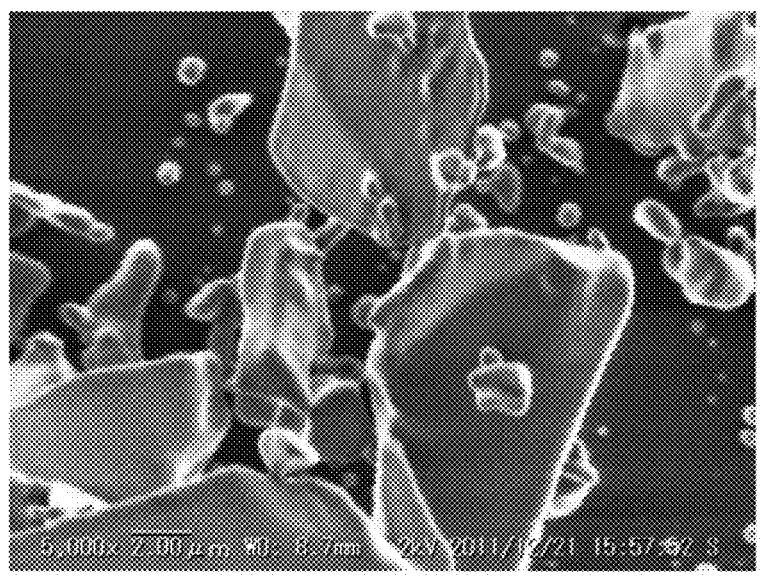

Here, FIG. 14 through FIG. 21 are electron microscope (SEM) photographs of the condition of Pr:LuAG crystal grains of the light-emitting layer. In these figures, (a) shows the condition before heat treatment, and (b) shows the condition after heat treatment at the same location as (a). FIG. 15 is an enlarged photograph of FIG. 14, FIG. 17 is an enlarged photograph of FIG. 16, FIG. 19 is an enlarged photograph of FIG. 18, and FIG. 21 is an enlarged photograph of FIG. 20.

With reference to FIG. 14 to FIG. 21, it is understood that in the Pr:LuAG crystal grains after heat treatment, as compared to those before heat treatment, the surface melts and then solidifies again. Particularly, when the A portion in FIG. 18(*a*) and the A portion in FIG. 18(*b*) are compared, it is clearly understood that the surfaces of the crystal grains melt and become round, and the crystal grains thus become smaller. In other words, in the light-emitting layer after the heat treatment, the crystalline melting layer that was melted by heat treatment and then solidified again covers the surface of the Pr:LuAG crystal grains. And, due to the fusion of the crystalline melting layers of the adjacent Pr:LuAG crystal grains, the Pr:LuAG crystal grains are tightly bound with each other, and therefore, the mechanical strength of the light-emitting layer can be increased without using the above-described binder.

Figure 22:
FIG. 22 is a SEM photograph of a surface of the sapphire substrate after peeling off the light-emitting layer.
Figure 22:
Figure 23:
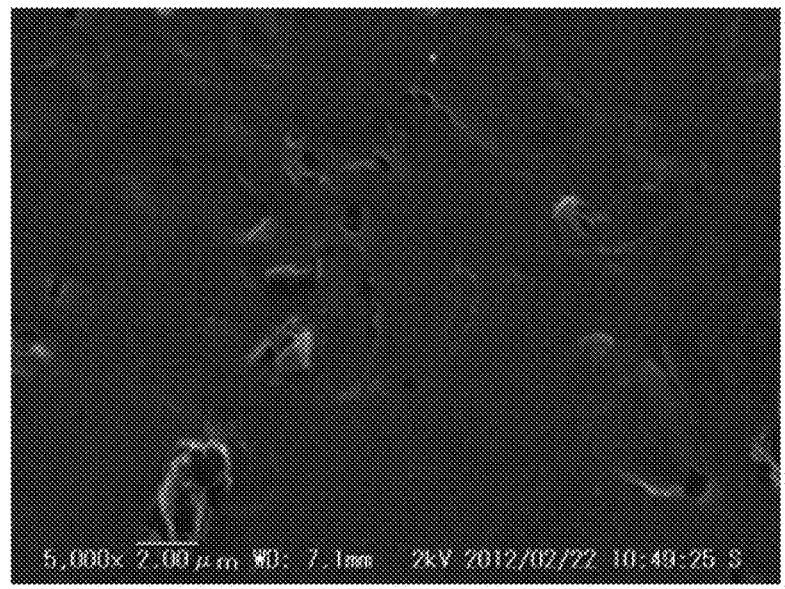
FIG. 23 is a SEM photograph of a surface of the sapphire substrate after peeling off the light-emitting layer.
Figure 23:
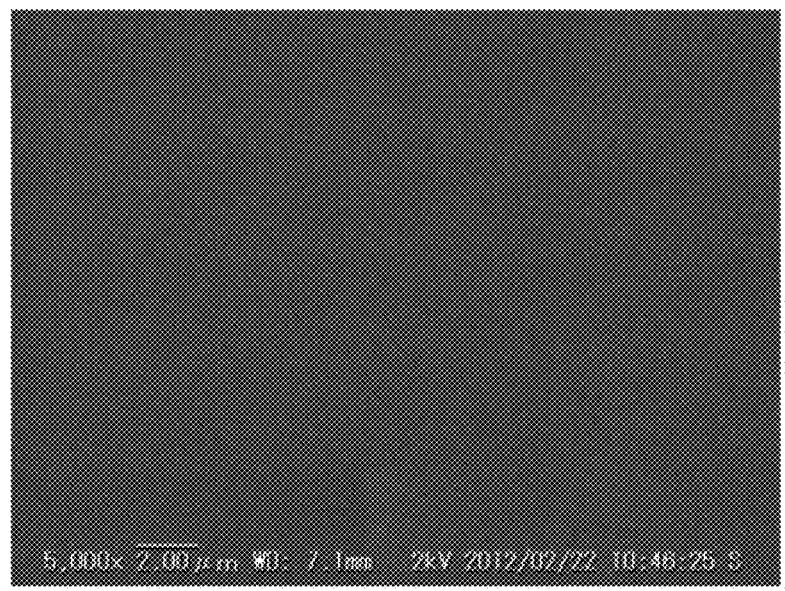

In addition, the crystalline melting layer described above also contributes to the binding between the Pr:LuAG crystal grains and the substrate. FIG. 22 and FIG. 23 are electron microscope (SEM) photographs of a surface of the sapphire substrate after peeling off the light-emitting layer. In these figures, (a) shows a case of peeling off the light-emitting layer formed by heat treatment, and (b) shows a case of peeling off the light-emitting layer formed with using a binder (heat treatment is not performed). In the present example, the light-emitting layer was removed by strongly rubbing the light-emitting layer with a BEMCOT (registered trademark).

With reference to FIG. 22(*a*) and FIG. 23(*a*), when the light-emitting layer formed by heat treatment is peeled off, the Pr:LuAG crystals cannot be removed completely, and the crystalline melting layer of the Pr:LuAG crystals remains on the surface of the sapphire substrate. On the other hand, with reference to FIG. 22(*b*) and FIG. 23(*b*), when the light-emitting layer formed by using a binder (heat treatment is not performed) is peeled off, the Pr:LuAG crystals can be removed completely, and only the surface of the sapphire substrate is shown. From these SEM photographs, it is understood that in the light-emitting layer formed by heat treatment, due to the fusion of the crystalline melting layer with the surface of the substrate, the Pr:LuAG crystal grains and the substrate are bound more strongly, and peeling of the light-emitting layer is suppressed.

In the present example, the temperature of heat treatment for the light-emitting layer was set to 1600° C. The temperature of heat treatment is preferably 1400° C. or more, and 2000° or less. Due to the fact that the temperature of heat treatment is 1400° C. or more, the crystalline melting layer on the surface of the Pr:LuAG crystal grains is formed at a sufficient thickness, the adhesion between the crystal grains themselves and between the crystal grains and substrate can be improved, and peeling of the light-emitting layer at the time of irradiation of the electron beam can be prevented effectively. Also, due to the fact that the temperature of heat treatment is 2000° C. or less, the changes in the crystalline structure of Pr:LuAG can be suppressed, and a decline in the luminous efficiency can be prevented. Furthermore, the deformation of the substrate (particularly, the sapphire substrate) can be prevented.

The ultraviolet light generating target, the electron-beam-excited ultraviolet light source, and the method for producing the ultraviolet light generating target according to the present invention are not limited to the above-described embodiment, and various other modifications are possible. For example, in the embodiment and each of the examples described above, an aluminum film is deposited on the light-emitting layer by evaporation. However, the aluminum layer may be omitted in the embodiment and each of the examples described above. Also, the aluminum film functions as an antistatic conductive film, and a conductive film other than aluminum may be used.

INDUSTRIAL APPLICABILITY

The present invention can be used as an ultraviolet light generating target, an electron-beam-excited ultraviolet light source, and a method for producing the ultraviolet light generating target, with which it is possible to improve the ultraviolet light generating efficiency.

REFERENCE SIGNS LIST

10 . . . electron-beam-excited ultraviolet light source, 11 . . . container, 12 . . . electron source, 13 . . . extraction electrode, 16 . . . power supply unit, 20 . . . ultraviolet light generating target, 21 . . . substrate, 21*a* . . . main surface, 21*b* . . . back surface, 22 . . . light-emitting layer, 23 . . . aluminum film, EB . . . electron beam, UV . . . ultraviolet light.

The invention claimed is:

1. An electron-beam-excited ultraviolet light source, comprising:
   an ultraviolet light generating target including a substrate made of sapphire, quartz, or rock crystal, and a light-emitting layer provided on the substrate and generating ultraviolet light upon receiving an electron beam;
   an electron source providing an electron beam to the ultraviolet light generating target; and
   a vacuum-pumped container in which the ultraviolet light generating target and the electron source are arranged, wherein
   the light-emitting layer includes powdered or granular Pr:LuAG crystals,
   the electron beam is incident on the light-emitting layer through a conductive film, and
   the ultraviolet light generated in the light-emitting layer output from the substrate.

2. The electron-beam-excited ultraviolet light source according to claim 1, wherein a thickness of the light-emitting layer is 0.5 μm or more and 30 μm or less.

3. The electron-beam-excited ultraviolet light source according to claim 1, wherein a median diameter of the Pr:LuAG crystals in the light-emitting layer is 0.5 μm or more and 30 μm or less.

4. The electron-beam-excited ultraviolet light source according to claim 1, wherein a surface of the Pr:LuAG crystals is covered with a crystalline melting layer that is melted by heat treatment and then solidified again.

5. The electron-beam-excited ultraviolet light source according to claim 4, wherein, by the crystalline melting layer, the Pr:LuAG crystals fuse with each other, and the Pr:LuAG crystals and the substrate also fuse with each other.

6. A method for producing an electron-beam-excited ultraviolet light source, wherein by depositing powdered or granular Pr:LuAG crystals on a substrate made of sapphire, quartz, or rock crystal, and then performing heat treatment for the Pr:LuAG crystals, a surface of the Pr:LuAG crystals is melted and then solidified again to form a crystalline melting layer, and wherein a light-emitting layer including the powdered or granular Pr:LuAG crystals is provided on the substrate, and ultraviolet light is generated upon receiving an electron beam.

7. The method for producing the electron-beam-excited ultraviolet light source according to claim 6, wherein the temperature of the heat treatment is 1400° C. or more and 2000° C. or less.

8. An ultraviolet light generating target, comprising:
a substrate made of sapphire, quartz, or rock crystal; and
a light-emitting layer provided on the substrate and generating ultraviolet light upon receiving an electron beam, wherein
the light-emitting layer includes powdered or granular Pr:LuAG crystals, and
a surface of the Pr:LuAG crystals is covered with a crystalline melting layer that is melted by heat treatment and then solidified again.

9. The ultraviolet light generating target according to claim 8, wherein, by the crystalline melting layer, the Pr:LuAG crystals fuse with each other, and the Pr:LuAG crystals and the substrate also fuse with each other.

10. The ultraviolet light generating target according to claim 8, wherein a thickness of the light-emitting layer is 0.5 μm or more and 30 μm or less.

11. The ultraviolet light generating target according to claim 8, wherein a median diameter of the Pr:LuAG crystals in the light-emitting layer is 0.5 μm or more and 30 μm or less.

\* \* \* \* \*